(12) United States Patent
Isaacson et al.

(10) Patent No.: US 9,044,237 B2
(45) Date of Patent: Jun. 2, 2015

(54) SECUREMENT STRUCTURE FOR JOINING MEDICAL DEVICE PARTS

(71) Applicants: Brad M. Isaacson, Lancaster, MA (US); Oscar R. Carrillo, Jr., Attleboro, MA (US); Jason Romano, Wakefield, RI (US)

(72) Inventors: Brad M. Isaacson, Lancaster, MA (US); Oscar R. Carrillo, Jr., Attleboro, MA (US); Jason Romano, Wakefield, RI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 13/791,288

(22) Filed: Mar. 8, 2013

(65) Prior Publication Data

US 2013/0274765 A1 Oct. 17, 2013

Related U.S. Application Data

(60) Provisional application No. 61/624,696, filed on Apr. 16, 2012.

(51) Int. Cl.
| | |
|---|---|
| *A61B 17/04* | (2006.01) |
| *A61B 17/12* | (2006.01) |
| *A61B 17/10* | (2006.01) |
| *F16B 17/00* | (2006.01) |
| *A61B 17/42* | (2006.01) |
| *A61B 17/46* | (2006.01) |
| *A61D 1/10* | (2006.01) |
| *A61B 1/00* | (2006.01) |
| *A61B 17/00* | (2006.01) |

(52) U.S. Cl.
CPC ........... *A61B 17/12013* (2013.01); *F16B 17/00* (2013.01); *Y10T 29/49826* (2015.01); *Y10T 403/7075* (2015.01); *A61B 1/0014* (2013.01); *A61B 2017/00296* (2013.01); *A61B 2017/00486* (2013.01); *A61B 2017/12018* (2013.01)

(58) Field of Classification Search
CPC ............. A61B 1/00121; A61B 1/0014; A61B 1/00137
USPC .......... 600/114, 125, 127, 175, 585; 606/148, 606/139–141, 144–147; 277/575, 924
See application file for complete search history.

(56) References Cited

U.S. PATENT DOCUMENTS 2,208,482 A * 7/1940 Victor ........................... 277/569
5,259,366 A 11/1993 Reydel et al.
5,269,789 A 12/1993 Chin et al.
(Continued)

FOREIGN PATENT DOCUMENTS

DE 10 2010 028 049 10/2011
JP 10-295624 * 4/1997 ............... A61B 1/00

OTHER PUBLICATIONS

Wilson-Cook Medical, "Duette Multi-Band Mucosectomy Device," Instructions for Use, pp. 1-7 (2005).

*Primary Examiner* — Todd Manahan
*Assistant Examiner* — Charles A Lutzow, III
(74) *Attorney, Agent, or Firm* — Fay Kaplun & Marcin, LLP

(57) ABSTRACT

A securement structure is positioned inside a channel of a first medical device to facilitate securement of the first medical device to a second medical device. The first medical device may be a ligation banding cap, and the second medical device may be an endoscope. The securement structure is adapted to be compressed between the second medical device and the first medical device to secure them together. This allows parts of different sizes to fit together.

20 Claims, 5 Drawing Sheets

(56) References Cited

U.S. PATENT DOCUMENTS

| | | | |
|---|---|---|---|
| 5,356,416 A | 10/1994 | Chu et al. | |
| 5,398,844 A | 3/1995 | Zaslavsky et al. | |
| 5,695,448 A * | 12/1997 | Kimura et al. | 600/121 |
| 5,707,343 A * | 1/1998 | O'Hara et al. | 600/121 |
| 5,853,416 A | 12/1998 | Tolkoff | |
| 5,857,585 A | 1/1999 | Tolkoff et al. | |
| 5,913,865 A | 6/1999 | Fortier et al. | |
| 5,968,056 A | 10/1999 | Chu et al. | |
| RE36,629 E | 3/2000 | Zaslavsky et al. | |
| 6,059,798 A * | 5/2000 | Tolkoff | 606/140 |
| 6,188,138 B1 * | 2/2001 | Bodo et al. | 257/778 |
| 6,235,040 B1 | 5/2001 | Chu et al. | |
| 7,736,302 B2 * | 6/2010 | Matsuno | 600/127 |
| 8,317,684 B2 * | 11/2012 | Matsuo et al. | 600/140 |
| 8,585,715 B2 * | 11/2013 | Hoffman et al. | 606/140 |
| 2001/0021596 A1 * | 9/2001 | Tamura | 439/66 |
| 2008/0091218 A1 | 4/2008 | Richardson | |
| 2008/0108874 A1 * | 5/2008 | Waller et al. | 600/178 |
| 2008/0255412 A1 * | 10/2008 | Surti | 600/104 |
| 2011/0077643 A1 * | 3/2011 | Dahla et al. | 606/41 |
| 2011/0152612 A1 * | 6/2011 | Trusty et al. | 600/109 |

* cited by examiner

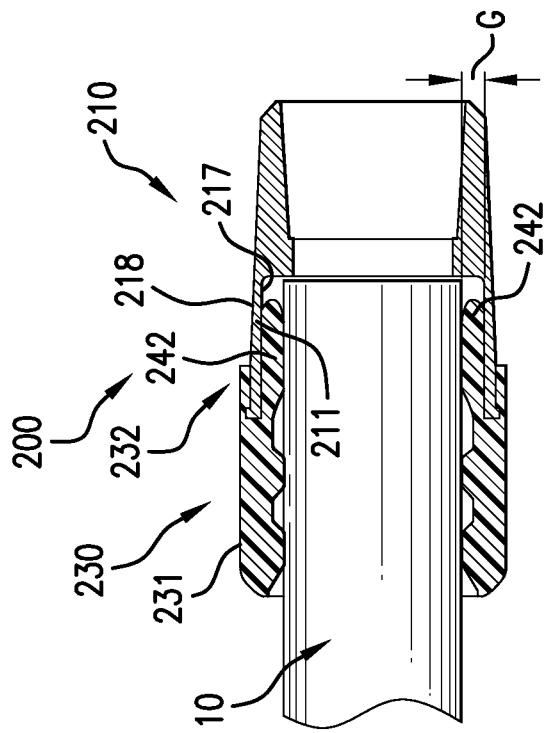
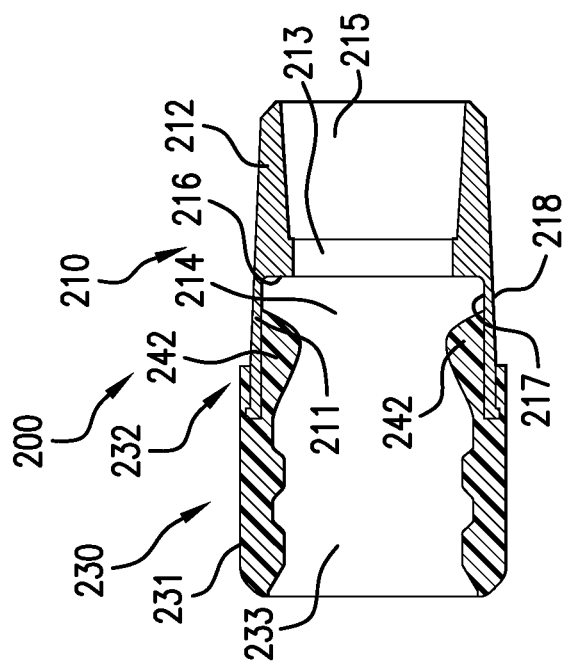
FIG.2A
FIG.2B

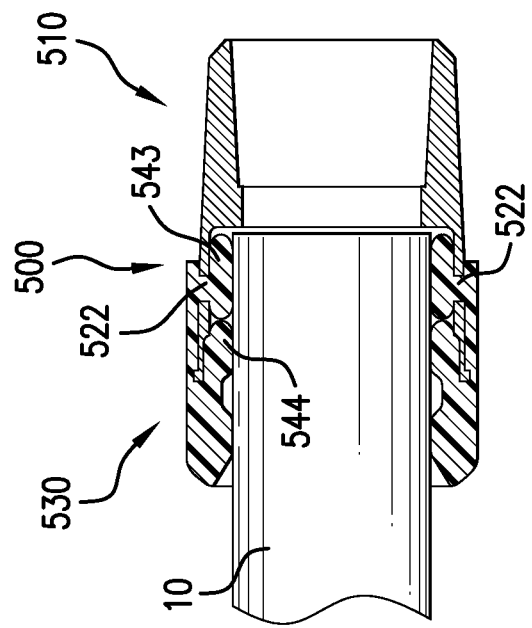
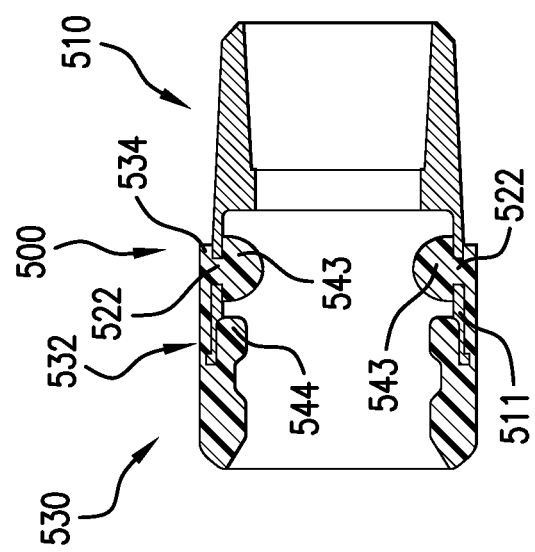

SECUREMENT STRUCTURE FOR JOINING MEDICAL DEVICE PARTS

CROSS REFERENCE TO RELATED APPLICATION

The present application claims priority to U.S. provisional application Ser. No. 61/624,696 filed Apr. 16, 2012, the disclosure of which is incorporated herein by reference in its entirety.

TECHNICAL FIELD

The invention relates to structures and methods for joining parts together. In some embodiments, the invention relates to a securement structure for joining a ligation banding cap to an endoscope or the like.

BACKGROUND OF THE INVENTION

Various medical procedures involve the use of medical devices that are joined together. For example, certain medical procedures involve the attachment of devices to the end of an endoscope or the like.

One example of a medical procedure that can involve the use of an endoscope is a ligation procedure. Ligation is a medical procedure whereby a physician ties off or mechanically constricts a piece of body tissue with a ligature such as a suture, clip or band. In certain procedures, the purpose of ligation may be to impede or obstruct the flow of blood, fluids and/or other bodily materials through the tissue. For example, a physician can remove target tissue by ligating it to obstruct circulation through the target tissue, thereby causing the tissue to die and slough off. The purpose of ligation may also be to hold tissue to be cauterized or resected, as in an endoscopic mucosal resection (EMR) procedure.

For ligating tissue inside a body cavity, orifice or lumen, physicians often use an endoscope to access the target tissue and ligate it. In one such form of endoscopic ligation, the physician attaches a ligation banding cap to the end of an endoscope. One or a plurality of ligation bands are stretched around the ligation banding cap and can be deployed by the physician. The physician uses the endoscope to position each stretched ligation band over the target tissue and then releases the band onto the tissue so that the band contracts and catches the tissue. The inward pressure of the ligation band constricts the target tissue.

Ligating instruments have been the subject of a number of patents and patent applications, including U.S. Pat. No. 5,259,366 to Reydel, et al.; U.S. Pat. No. 5,269,789 to Chin, et al.; U.S. Pat. No. 5,356,416 to Chu, et al.; U.S. Pat. No. 5,398,844 to Zaslavsky, et al.; U.S. Pat. No. 5,853,416 to Tolkoff; U.S. Pat. No. 5,857,585 to Tolkoff, et al.; U.S. Pat. No. 5,913,865 to Fortier, et al.; U.S. Pat. No. 5,968,056 to Chu, et al., U.S. Pat. No. 6,235,040 to Chu, et al.; U.S. Pat. No. RE 36,629 to Zaslavsky, et al., and U.S. Patent Application Publication No. 2008/0091218 to Richardson. The disclosures of these prior U.S. patents and patent application are expressly incorporated herein by reference.

In certain previous ligating instruments, the ligation banding cap is designed for use with endoscopes of a particular size. The ligation banding cap assembly includes an adapter for fitting on the end of the endoscope. Generally, however, such prior ligation banding cap assemblies were not suitable for fitting on a wide range of endoscope sizes.

There remains a need for improving the attachment together of medical devices. In some instances, prior means for joining medical devices together has had the potential to lead to problems such as misalignment, instability, jarring, inadequate sealing, poor suction, poor visualization, separation of parts and/or other issues arising from a poor connection. The potential for these problems is exacerbated when parts of different sizes are joined together. There remains a need for facilitating the joining of different-sized parts together while avoiding or minimizing these potential problems.

SUMMARY OF THE INVENTION

The present disclosure relates to the use of a securement structure that is positioned inside of a channel of a first medical device, wherein a second medical device is received within the channel, and the securement structure is compressed between the first and second medical devices to facilitate securement of the first medical device to the second medical device.

In accordance with some embodiments, an adapter is provided for joining a first medical device to a second medical device. The adapter comprises a securement structure comprising one or more resilient securement projections positionable inside the channel of the first medical device. The securement structure is adapted to be compressed between the second medical device and a mounting structure of the first medical device when the second medical device is received within the channel of the first medical device. The resilient securement projections may comprise one or more resilient lobes, rings, ridges, domes, bumps, wedges and/or any other suitable projections.

In accordance with other embodiments, a cap assembly comprises a cap and a securement structure. The cap comprises a mounting structure defining a channel, the mounting structure at least partially surrounding the channel. The securement structure comprises one or more resilient securement projections located inside the channel of the cap, adjacent an inner surface of the mounting structure. The securement structure is adapted to be compressed between an outer surface of an elongated medical device and the inner surface of the mounting structure of the cap when the elongated medical device is received within the channel of the cap. The elongated medical device may be an endoscope. The cap assembly may be a ligation banding cap assembly.

The cap may further comprise one or more grooves in the inner surface of the mounting structure, the one or more grooves adapted to receive the one or more resilient securement projections. The cap may further comprise one or more holes in the mounting structure, the one or more holes adapted to receive the one or more resilient securement projections. The securement structure may be part of an adapter that is configured to be received around the elongated medical device.

In accordance with other embodiments, a method of securing a cap assembly to an end of an elongated medical device is provided. The method comprises positioning the cap assembly with respect to the elongated medical device and placing the cap assembly on the end of the elongated medical device. When the cap assembly is placed on the end of the elongated medical device, the securement structure is compressed between an outer surface of the elongated medical device and the inner surface of the mounting structure of the cap, such that the securement structure secures the cap to the end of the elongated medical device.

BRIEF DESCRIPTION OF THE DRAWINGS

FIG. 2A shows an example of one embodiment of a ligation banding cap assembly with a resilient securement structure inside the channel of the cap.

FIG. 2B shows the ligation banding cap assembly of FIG. 2A mounted on the end of an endoscope.

FIG. 5A shows an example of another embodiment of a ligation banding cap assembly with a resilient securement structure inside the channel of the cap.

FIG. 5B shows the ligation banding cap assembly of FIG. 5A mounted on the end of an endoscope.

DETAILED DESCRIPTION

Figure 1B:
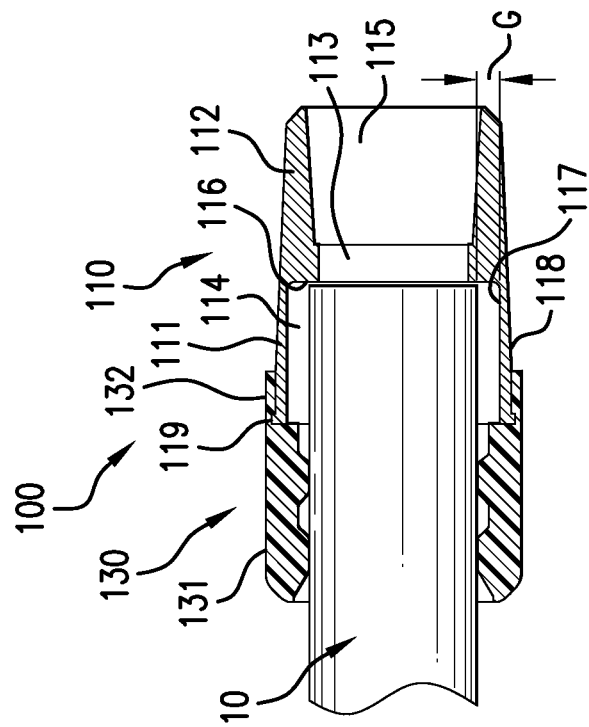
FIG. 1B shows the ligation banding cap assembly of FIG. 1A mounted on the end of an endoscope.
Figure 1A:
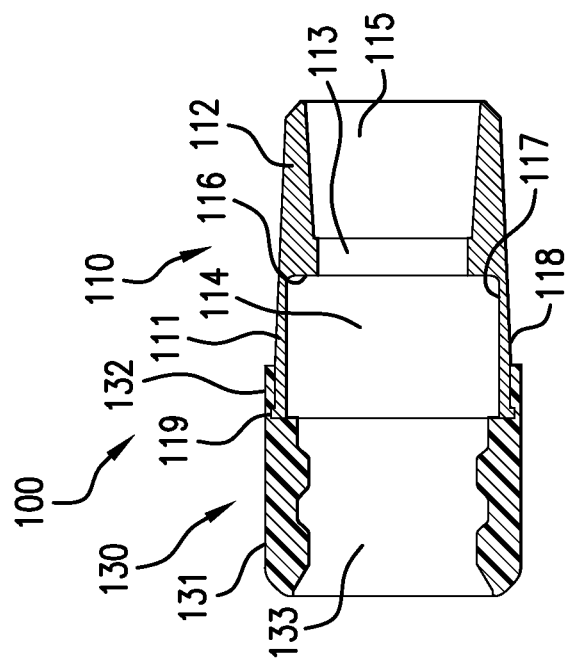
FIG. 1A shows an example of a prior art ligation banding cap assembly.

FIG. 1A shows a side cross-sectional view of a prior art ligation banding cap assembly 100. The ligation banding cap assembly 100 includes a cap 110 and an adapter 130. The cap 110 is made of a relatively rigid polymeric material such as polycarbonate. The adapter 130 is made of a resilient elastomeric material.

The cap 110 comprises a proximal portion or endoscopic mounting structure 111 and a distal portion 112. A channel 113 extends through the length of the cap 110, through both the mounting structure 111 and the distal portion 112. The channel 113 comprises a proximal channel portion 114 and a distal channel portion 115. An abutment surface 116 defines a stop for advancement of an endoscope to be placed within proximal channel portion 114.

The mounting structure 111 comprises an inner surface 117 and an outer surface 118. A lip 119 projects from the outer surface 118 and serves to help secure the adapter 130 on the cap 110.

The adapter 130 is adapted to be joined to the cap 110 as shown. The adapter 130 comprises a proximal portion 131 and a distal portion 132. A channel 133 extends through the length of the adapter 130, through both the proximal portion 131 and the distal portion 132.

The prior art ligation banding cap assembly 100 is adapted for placement on an endoscope that has a diameter that is substantially the same as or only slightly less than the inner diameter of the mounting structure 111 of the cap 110. In this way, when the ligation banding cap assembly 100 is placed on the distal end of such an endoscope, the cap 110 fits snugly on the endoscope. In addition, the proximal portion 131 of the adapter 130 is stretched so that its inner diameter can accommodate the endoscope. The tendency of the resilient material of the adapter 130 to want to return to its resting shape and size creates a snug fit of the proximal portion 131 of the adapter 130 around the outside surface of the endoscope.

The prior art ligation banding cap assembly 100 is not well-suited, however, to be placed on an endoscope that has a diameter that is substantially less than the inner diameter of the mounting structure 111 of the cap 110. This is illustrated in FIG. 1B. FIG. 1B shows a side cross-sectional view of the ligation banding cap assembly 100 of FIG. 1A mounted on an endoscope 10 that has a diameter that is substantially less than the inner diameter of the mounting structure 111 of the cap 110. As can be seen in FIG. 1B, this difference in diameter leads to a gap G, and the fit between the cap 110 and the endoscope 10 is not snug. This poor fit has had the potential to lead to problems such as misalignment between the cap and the endoscope, instability of the cap, jarring of the cap during positioning, inadequate sealing between the cap and the endoscope, poor transfer of suction from the endoscope through the cap, poor visualization due to relative movement of parts, separation of the cap and endoscope, incorrect or incomplete deployment of a band, inadequate medical treatment and/or other issues arising from a poor connection. In addition, such a design requires different sizes of cap assemblies for different-sized endoscopes, which can increase design and manufacturing costs, can necessitate stocking of multiple different parts, can lead to a mix-up of parts, and can create inventory control problems. For example, because different sizes can be used at different rates, a hospital may run out of one size more quickly than others, and a particular size may be unavailable when needed.

FIG. 2A shows a side cross-sectional view of an example of one embodiment of a ligation banding cap assembly with a resilient securement structure inside the channel of the cap. The ligation banding cap assembly 200 includes a cap 210 and an adapter 230. The cap 210 is made of a relatively rigid polymeric material. The adapter 230 is made of a resilient elastomeric material.

The cap 210 comprises a proximal portion or endoscopic mounting structure 211 and a distal portion 212. A channel 213 extends through the length of the cap 210, through both the mounting structure 211 and the distal portion 212. The channel 213 comprises a proximal channel portion 214 and a distal channel portion 215. An abutment surface 216 defines a stop for advancement of an endoscope to be placed within proximal channel portion 214. The mounting structure 211 comprises an inner surface 217 and an outer surface 218.

The adapter 230 is adapted to be joined to the cap 210 as shown. The adapter 230 comprises a proximal portion 231 and a distal portion 232. A channel 233 extends through the length of the adapter 230, through both the proximal portion 231 and the distal portion 232.

The distal portion 232 of the adapter 230 differs significantly from the distal portion 131 of the adapter 130. The distal portion 232 of the adapter 230 comprises a securement structure having one or more securement projections. In the example of FIG. 2A, the securement projections are in the form of resilient lobes 242. The resilient lobes 242 extend distally from the proximal portion 231 of the adapter 230 and are positioned in the proximal channel portion 214 of channel 213, along the inner diameter of the mounting structure 211. As can be seen in FIG. 2A, the resilient lobes 242 are adjacent to the inner surface 217 of the mounting structure 211.

The resilient securement structure that is positioned, at least in part, inside the channel of the mounting structure of the cap allows the cap assembly to fit securely to endoscopes of various sizes. At rest, the securement structure defines an inner diameter that is substantially smaller than the inner diameter of the mounting structure. Accordingly, when the cap assembly is assembled to an endoscope with a relatively small diameter, the endoscope will contact and compress the securement structure to create a snug fit. That is, when the cap assembly is placed on the end of the endoscope, the securement structure is compressed between an outer surface of the endoscope and the inner surface of the mounting structure of the cap. The compression of the resilient elastomeric material of the securement structure from its resting size and shape creates forces against the endoscope and cap that secure the cap to the endoscope.

FIG. 2B shows a side cross-sectional view of the ligation banding cap assembly 200 of FIG. 2A mounted on an endoscope 10 that has a diameter that is substantially less than the inner diameter of the mounting structure 211 of the cap 210. As can be seen in FIG. 2B, this difference in diameter leads to a gap G. However, the securement structure comprising the resilient lobes 242 is positioned in that gap G. Because of the securement structure positioned inside the mounting structure 211 of the cap 210, the fit between the cap 210 and the endoscope 10 is snug.

It will be appreciated that the use of a securement structure positioned inside the mounting structure of a cap as described herein can overcome the problems associated with a poor fit as described above. In addition, the design enables the use of a single size of cap assembly for different-sized endoscopes. Thus, the design shown in FIGS. 2A and 2B can accommodate a relatively small-diameter endoscope as shown, as well as larger ones, including endoscopes having a diameter substantially the same or slightly less than the diameter of the mounting structure. With the larger endoscopes, the securement structure is more compressed, thereby yielding to accommodate the larger size. Such a design has advantages in reducing design and manufacturing costs, avoiding the need to stock multiple different parts, avoiding a potential mix-up of parts, and avoiding the above-described inventory control problems.

Figure 3B:
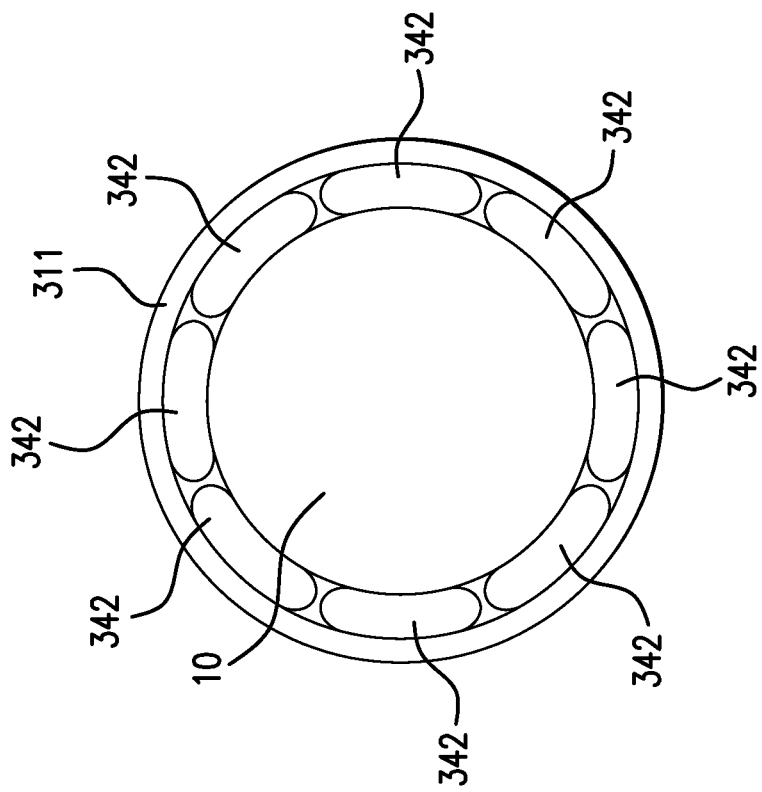
FIG. 3B shows the ligation banding cap assembly of FIG. 3A mounted on the end of an endoscope.
Figure 3A:
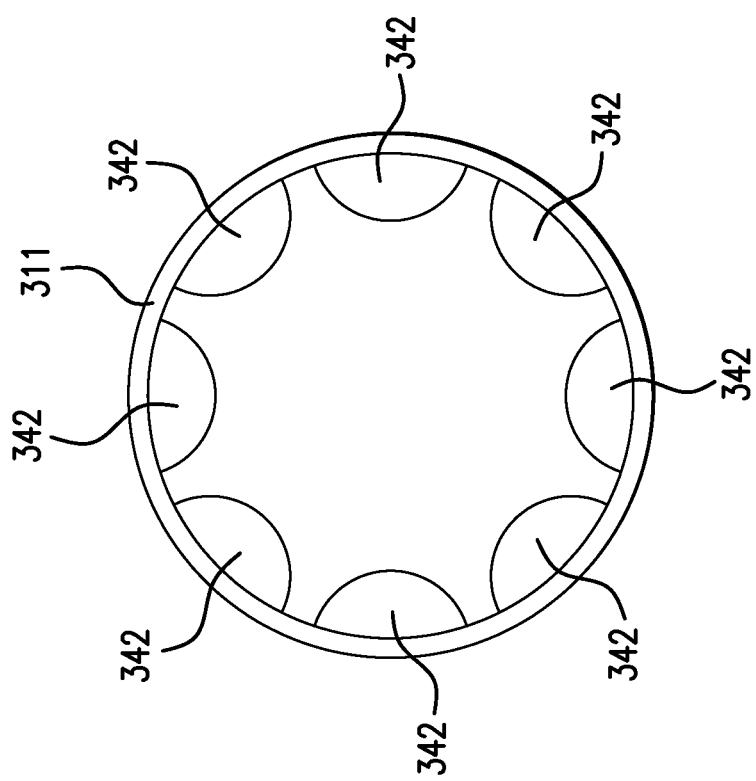
FIG. 3A shows a cross-sectional view of a ligation banding cap assembly with a resilient securement structure inside the channel of the cap.

FIG. 3A shows a cross-sectional view of a ligation banding cap assembly with a resilient securement structure inside the channel of the cap. The cross-section is taken through the mounting structure 311 of the cap, where the resilient lobes 342 of the securement structure are positioned. As can be seen in FIG. 3A, each of the resilient lobes 342 can be a discrete part that projects from the proximal portion of the adapter. In alternate embodiments, the adapter material can form a complete tube inside the channel of the mounting structure, and the resilient projections such as lobes can project inwardly from the tube. The resilient projections can alternatively be rings, ridges, domes, bumps, wedges and/or any other suitable structures that project inwardly into the channel of the mounting structure in order to define a smaller diameter so as to accommodate smaller endoscopes or other devices. The resilient projections, e.g., the lobes, rings, ridges, domes, bumps, wedges and/or other suitable structures, can be tapered from the proximal end (into which the endoscope or other device is inserted) to the distal end, which can help facilitate attachment to the endoscope or other device. In one example, the lobes may be long fingers that fold, bend or buckle, in addition to being compressed, when the attachment is made to the endoscope or other device, thereby facilitating the interference fit.

In FIG. 3A, eight projections are shown. More or fewer projections may be used. In one example, the projection can be a single raised ring that extends around the channel. In another example, the projection can be a single helical ridge that extends around the channel. The securement structure can comprise one or a plurality of lobes, rings, ridges, domes, bumps, wedges and/or any other suitable projections.

FIG. 3B shows the ligation banding cap assembly of FIG. 3A mounted on the end of an endoscope 10. As can be seen in FIG. 3B, when the cap assembly is placed on the end of the endoscope 10, the resilient lobes 342 of the securement structure are compressed between an outer surface of the endoscope 10 and the inner surface of the mounting structure 311 of the cap. In this manner, the securement structure secures the cap to the end of the endoscope.

Figure 4A:
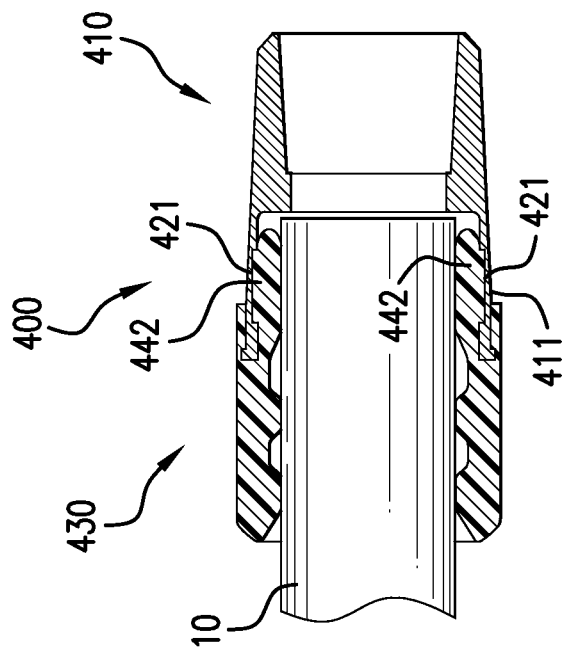
FIG. 4A shows an example of another embodiment of a ligation banding cap assembly with a resilient securement structure inside the channel of the cap.

FIG. 4A shows a side cross-sectional view of another example of an embodiment of a ligation banding cap assembly with a resilient securement structure inside the channel of the cap. The ligation banding cap assembly 400 includes a cap 410 and an adapter 430. The cap 410 is made of a relatively rigid polymeric material. The adapter 430 is made of a resilient elastomeric material.

The ligation banding cap assembly 400 is similar to the ligation banding cap assembly 300 except that the cap 410 includes a plurality of grooves 421 along its inner surface. The cap 410 may have a groove for each resilient lobe 442. Each resilient lobe 442 is designed in such a way that when it is compressed, part of the material of the resilient lobe 442 moves into the corresponding groove 421. This can help relieve the pressure when larger endoscopes are used.

Figure 4B:
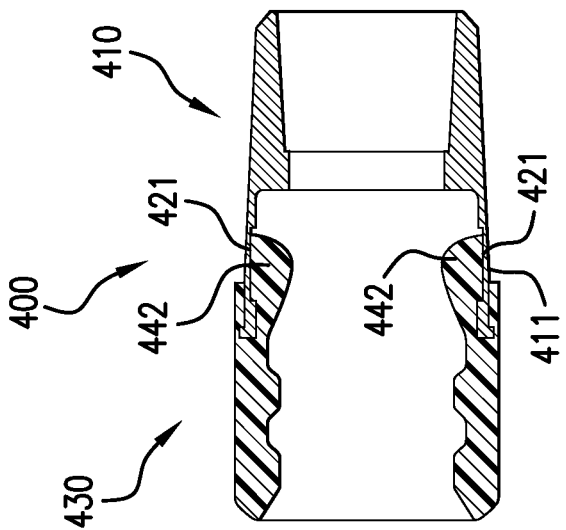
FIG. 4B shows the ligation banding cap assembly of FIG. 4A mounted on the end of an endoscope.

FIG. 4B shows a side cross-sectional view of the ligation banding cap assembly 400 of FIG. 4A mounted on an endoscope 10. As can be seen in FIG. 4B, when the cap assembly 400 is placed on the end of the endoscope 10, the securement structure is compressed between an outer surface of the endoscope 10 and the inner surface of the mounting structure 411 of the cap 410. Part of the material of each resilient lobe 442 moves into its corresponding groove 421. This can help facilitate a snug and secure fit between the cap 410 and the endoscope 10.

FIG. 5A shows a side cross-sectional view of another example of an embodiment of a ligation banding cap assembly with a resilient securement structure inside the channel of the cap. The ligation banding cap assembly 500 includes a cap 510 and an adapter 530. The cap 510 is made of a relatively rigid polymeric material. The adapter 530 is made of a resilient elastomeric material.

The ligation banding cap assembly 500 is similar in some respects to the ligation banding cap assembly 400. The cap 510 includes a plurality of holes 522 in the mounting structure 511. The distal portion 532 of the adapter 530 includes an outer portion 534 that extends to an area over the holes 522. The securement structure comprises a series of resilient domes 543, with one dome adjacent each hole 522. The material of the adapter 530 extends through the holes 522 to connect the outer portion 534 of the adapter to the resilient domes 543. The holes 522 may be slightly larger than the material of the adapter extending through the holes 522. In this way, when the resilient domes 543 are compressed, part of the material of the resilient domes 543 can move into the holes 522.

In the cap assembly 500, the distal portion 532 of the adapter 530 also includes a resilient ring 544 positioned inside the channel of the mounting structure 511. Thus, in this embodiment, the securement structure inside the channel of the mounting structure 511 comprises the resilient domes 543 and the resilient ring 544.

FIG. 5B shows a side cross-sectional view of the ligation banding cap assembly 500 of FIG. 5A mounted on an endoscope 10. As can be seen in FIG. 5B, when the cap assembly 500 is placed on the end of the endoscope 10, the securement structure is compressed between an outer surface of the endoscope 10 and the inner surface of the mounting structure 511 of the cap 510. That is, the resilient domes 543 and the resilient ring 544 are compressed, thereby facilitating a snug and secure fit between the cap 510 and the endoscope 10.

As an alternative to holes 522 as shown, the cap or first medical device may include cut-outs, shapes, slots, wells, etc., through which the resilient material of the securement structure may extend, connect or protrude. As with the material through the holes 522, this can create a stronger connection between the resilient material of the securement structure and the more rigid material of the cap or first medical device.

It will be appreciated that a ligation banding cap assembly according to embodiments described above may accommodate a wide range of sizes of endoscopes. For example, a single ligation banding cap assembly can accommodate endoscopes having diameters from 8.8 mm to 11.6 mm. Other sizes can be made to accommodate other size ranges.

Embodiments other than those illustrated herein are of course possible. A securement structure as described also may be utilized for joining other medical devices together, other than a ligation banding cap to an endoscope. For example, other tools or devices can be mounted to other elongated devices, such as, but not limited to, catheters, other tubes and the like.

The securement structure, or the resilient securement projections, may be manufactured of any suitable resilient material that allows the resilient securement projections to function as described herein. Accordingly, suitable elastomers, foams or other materials may be used. The securement structure, or the resilient securement projections, may be coated so as to facilitate securement and sealing to the endoscope or other device (e.g., by increasing friction or tackiness) and/or to facilitate ease of attachment to the endoscope or other device (e.g., by providing lubrication or reducing friction). The securement structure, or the resilient securement projections, may have surface modifications, such as roughening, bumps, ridges, grooves, etc., so as to facilitate securement and sealing to the endoscope or other device and/or to facilitate ease of attachment to the endoscope or other device (e.g., the lobes may be roughened or provided with bumps in order to improve the connection). The securement structure, or the resilient securement projections, may be made of layers. For example, in one embodiment, the resilient securement projections may have an outer layer to provide tackiness and sealing to the endoscope or other device and an inner layer that provides suitable compressibility to create the secure attachment to the endoscope or other device. The first medical device or cap could be formed as one integral unit with the securement structure or resilient securement projections, for example with the first medical device or cap comprising a more rigid area of the unit and with the resilient securement projections comprising a more resilient area of the unit. The securement structure, or the resilient securement projections, may comprise one or more materials that swell upon contact with fluids, such as saline and/or body fluids. In this manner, the medical devices may be positioned together and then the fluid can be introduced to swell the resilient securement projections and create or improve the connection/seal.

The foregoing embodiments are merely examples of embodiments within the scope of the invention. Other embodiments are possible that incorporate one or more of the features and/or advantages of the above-described embodiments. This invention thus embraces other embodiments within the scope of the claims.

What is claimed is:

1. An adapter for joining a first medical device to a second medical device, wherein the first medical device is adapted to be secured to an end of the second medical device with the end of the second medical device received within a channel of the first medical device, the adapter comprising:
a securement structure comprising an outer portion and one or more resilient securement projections positionable inside the channel of the first medical device, the outer portion and the one or more resilient securement projections defining a space therebetween in which a mounting structure of the first medical device is receivable;
wherein the one or more resilient securement projections is adapted to be compressed between the second medical device and a mounting structure of the first medical device when the second medical device is received within the channel of the first medical device; and
wherein the securement structure secures the first medical device to the end of the second medical device.

2. The adapter of claim 1, wherein the one or more resilient securement projections comprises one or more resilient lobes, ridges or wedges.

3. The adapter of claim 1, wherein the one or more resilient securement projections comprises one or more resilient domes or bumps.

4. The adapter of claim 1, wherein the one or more resilient securement projections comprises one or more resilient rings.

5. The adapter of claim 1, wherein the securement structure comprises a material more resilient than the mounting structure of the first medical device against which the securement structure is adapted to be compressed.

6. A cap assembly adapted to be secured to an end of an elongated medical device, the cap assembly comprising:
a cap comprising a mounting structure defining a channel, the mounting structure at least partially surrounding the channel; and
a securement structure comprising an outer portion and one or more resilient securement projections located inside the channel of the cap, adjacent an inner surface of the mounting structure, the outer portion and the one or more resilient securement projections defining a space therebetween;
wherein the one or more resilient securement projections is adapted to be compressed between an outer surface of the elongated medical device and the inner surface of the mounting structure of the cap when the elongated medical device is received within the channel of the cap; and
wherein the securement structure secures the cap to the end of the elongated medical device.

7. The cap assembly of claim 6, wherein the elongated medical device is an endoscope.

8. The cap assembly of claim 6, wherein the cap assembly is a ligation banding cap assembly.

9. The cap assembly of claim 6, wherein the cap further comprises one or more grooves in the inner surface of the mounting structure, the one or more grooves adapted to receive the one or more resilient securement projections.

10. The cap assembly of claim 6, wherein the cap further comprises one or more holes in the mounting structure, the one or more holes adapted to receive the one or more resilient securement projections.

11. The cap assembly of claim 6, wherein the securement structure is part of an adapter that is configured to be received around the elongated medical device.

12. The cap assembly of claim 6, wherein the one or more resilient securement projections comprises one or more resilient lobes, ridges or wedges.

13. The cap assembly of claim 6, wherein the one or more resilient securement projections comprises one or more resilient domes or bumps.

14. The cap assembly of claim 6, wherein the one or more resilient securement projections comprises one or more resilient rings.

15. The cap assembly of claim 6, wherein the securement structure comprises a material more resilient than the mounting structure of the first medical device against which the securement structure is adapted to be compressed.

16. A method of securing a cap assembly to an end of an elongated medical device, comprising:
   positioning the cap assembly with respect to the elongated medical device, the cap assembly comprising:
      a cap comprising a mounting structure defining a channel, the mounting structure at least partially surrounding the channel; and
      a securement structure comprising an outer portion and one or more resilient securement projections located inside the channel of the cap, adjacent an inner surface of the mounting structure, the outer portion and the one or more resilient securement projections defining a space therebetween in which the mounting structure is received; and
   placing the cap assembly on the end of the elongated medical device, thereby compressing the securement structure between an outer surface of the elongated medical device and the inner surface of the mounting structure of the cap, such that the securement structure secures the cap to the end of the elongated medical device.

17. The method of claim 16, wherein the elongated medical device is an endoscope.

18. The method of claim 16, wherein the cap assembly is a ligation banding cap assembly.

19. The method of claim 16, wherein the securement structure is part of an adapter that is a part of the cap assembly and that is secured to the cap.

20. The method of claim 16, wherein the securement structure is part of an adapter that is received around the elongated medical device when the cap assembly is placed on the end of the elongated medical device.

* * * * *